United States Patent [19]

Surzycki et al.

[11] Patent Number: 5,610,010
[45] Date of Patent: Mar. 11, 1997

[54] PROCESS AND APPARATUS FOR FRAGMENTING BIOMATERIALS

[75] Inventors: Stefan J. Surzycki; Masahito Kityama; Robert K. Togasaki, all of Bloomington, Ind.

[73] Assignee: Indiana University Foundation, Bloomington, Ind.

[21] Appl. No.: 39,430

[22] PCT Filed: Oct. 11, 1991

[86] PCT No.: PCT/US91/07530

§ 371 Date: Mar. 7, 1994

§ 102(e) Date: Mar. 7, 1994

[87] PCT Pub. No.: WO92/07091

PCT Pub. Date: Apr. 30, 1992

Related U.S. Application Data

[63] Continuation-in-part of Ser. No. 660,650, Feb. 25, 1991, abandoned, which is a continuation-in-part of Ser. No. 595,429, Oct. 11, 1990, abandoned.

[51] Int. Cl.[6] .............................. C12Q 1/68; C12M 1/00; C12N 15/10
[52] U.S. Cl. .................................. 435/6; 239/338; 422/99; 422/243; 435/283.1; 435/285.1; 935/19
[58] Field of Search ........................... 435/6, 283.1, 287, 435/285.1; 422/99, 100, 101, 102, 243, 244; 536/22.1; 239/338; 935/19; 530/350

[56] References Cited

U.S. PATENT DOCUMENTS

| | | | |
|---|---|---|---|
| Re. 33,642 | 4/1991 | Lester | 128/200.21 |
| 4,161,282 | 7/1979 | Erb | 239/8 |
| 4,560,519 | 12/1985 | Cerny | 261/78.2 |
| 4,612,926 | 9/1986 | Boiarski | 128/200.21 |
| 4,805,609 | 2/1989 | Roberts et al. | 128/200.21 |
| 5,506,100 | 4/1996 | Surzycki et al. | 435/6 |

FOREIGN PATENT DOCUMENTS

| | | |
|---|---|---|
| 3905354 | 8/1990 | Germany . |
| 2227690 | 8/1990 | United Kingdom . |

OTHER PUBLICATIONS

Young et al. "Continuous Aerosol Therapy System Using a Modified Collision Nebulizer" J Clin Microbiol 5(2) 131–136 1977.
Hubbard et al. "Fate of areosolized recombinant DNA–Produced Antitrypsin . . . " PNAS 86: 680–684 1989.
Pays et al. "Location of Endogenous RNA Polymerase B . . . " FEBS Lett 61(2): 166–170.
Ordahl et al. "Sheared DNA fragment Sizing: Comparison of Techniques" Chem Abs. 86 #86-27523K 1977 p. 175.

*Primary Examiner*—Mindy Fleisher
*Assistant Examiner*—Nancy J. Degen
*Attorney, Agent, or Firm*—Woodard, Emhardt, Naughton Moriarty & McNett

[57] ABSTRACT

Described is an improved process for fragmenting a biomaterial and isolating and recovering a component thereof. The preferred improved process includes the step of performing the fragmentation by nebulizing a liquid medium containing the biomaterial. A preferred process for fragmenting isolated DNA includes the step of nebulizing a fluid containing the DNA. This preferred process provides randomness superior to prior known DNA fragmentation methods, as well as other important advantages. An improved nebulization device is also described.

29 Claims, 14 Drawing Sheets

COMPARISON OF NEBULIZATION WITH POTTER HOMOGENIZER
(SOYBEAN CELL CULTURE)

Legend:
- OD 280
- OD 260
- OD 652

X-axis: TYPE OF INSTRUMENT — POTTER (1 STROCK), POTTER (6 STROCKS), NEBULIZER (20 psi 1 min)

*Fig. 10*

PROCESS AND APPARATUS FOR FRAGMENTING BIOMATERIALS

CROSS-REFERENCE

This application is a continuation-in-part of U.S. Application Ser. No. 07/660,650, filed Feb. 25, 1991, now abandoned, which is a continuation-in-part of U.S. Patent Application Ser. No. 07/595,429, filed Oct. 11, 1990, now abandoned.

BACKGROUND

The present invention relates generally to fragmentable biomaterials, and more particularly to a highly effective process and apparatus for fragmenting such biomaterials, e.g., nucleic acids such as DNA, cells, starches, etc., and recovering components thereof. The invention thus holds great importance including to the heightened world-wide interest in biotechnology, genome research and related DNA sequencing efforts.

For some time there has been an interest in sequencing nucleic acids such as deoxyribonucleic acid (DNA). This interest stems from academic and commercial desires both to find out more about the general nature of nucleic acids and in particular that of human genome and genomes of commercially important plants or animals, and to identify potential DNA attributes which can lead to new medicines, treatments, and in some cases possibly even prevention of genetically-caused disorders. Successful DNA sequencing depends highly upon the ability to generate random DNA fragments from larger DNA molecules. Quite naturally, therefore, much interest and effort has been devoted to developing ways to fragment DNA in a random fashion.

In general, DNA sequencing includes three basic tasks. First, individual fragments to be sequenced are generated. Second, sequencing reactions are run on the fragments. Third, electrophoresis and compilation of data are completed. Success of the current large scale DNA sequencing efforts depends, to a large degree, on technological innovations in sequencing. In particular, such success is largely dependent on the development and implementation of automated procedures for all steps of DNA sequencing C. R. Cantor, *Orchestrating the Human Genome Project*, Science 248, 49 (1990). Presently, the second and third tasks have been automated or are currently in the process of being automated. See, for instance, L. Smith et al., *Fluorescence Detection an Automated DNA Sequence Analysis*, Nature 321, 674 (1986); J. M. Prober et al., *A System for Rapid DNA Sequencing with Fluorescent Chain-Terminating Dideoxynucleotides*, Science 238, 336 (1987); J. Zimmerman et al., *Automated Sanger Dideoxy Sequencing Reaction Protocol*, FEBS Letters 233, 432 (1988). However, the first step, frequently referred to as the "strategy of sequencing", has proven to be difficult to improve upon or automate.

The sequencing strategy that has been considered ideally suited to large scale, rapid DNA sequencing is the random or "shot gun" strategy. This strategy involves random subcloning of a large DNA fragment and the generation of a random-fragment sequencing library. As already stated, the success of this strategy depends largely on the degree of randomness of the fragments generated, and further how time consuming the fragmentation procedure is. To date, three methods have been used in significant amount to generate DNA fragments for the construction of sequencing libraries. A first method employs partial restriction enzyme digestions. A second involves fragmentation of DNA by DNas I enzyme in the presence of $Mn^{++}$, and a third method relies upon sonication to physically break DNA. Despite their significant use to date, each of these methods carries a number of disadvantages.

A major drawback of the first method, the use of restriction enzymes, stems from the non-random distribution of restriction sites along the DNA, which can lead to lack of the desired randomness in the clone bank. Countering this problem requires use of numerous different restriction enzymes in the preparation of sequencing banks, a laborious and time consuming process. This method also requires performing a number of carefully controlled restriction enzyme reactions that are difficult to reproduce with different enzymes and DNA preparations.

The second method, using DNase I, surmounts some of the difficulties in the first method because there is little DNA sequence specificity in DNase I cleavage. However, even to a larger extent than the first method, the application of DNase I to generate random fragments is difficult to reproduce, and requires numerous test reactions. This is wasteful and necessitates large amounts of starting material.

The third method, sonication, does carry an advantage in that it is easier to reproduce and control than either of the enzymatic methods discussed above. However, its application requires large amounts of starting material because only a small portion of the original DNA molecules are sheared to the required size. The sonication method also involves laborious calibration of the sonicator, and rigorous timing for subsequent treatments. Moreover, it has been shown that sonication shears AT-rich sequences preferentially, and thus does not create truly random sequencing libraries P. L. Deininger, *Random Subcloning of Sonicated DNA: Application to Shotgun DNA Sequence Analysis*, Analytical Biochemistry 129, 216 (1983). This can be particularly evident if the DNA to be sheared includes long AT and GC-rich stretches.

In countless other facets, interest and research in biotechnology has also increased dramatically in recent years. Much of this research requires the isolation and recovery of biomaterials found within cells. As such, obtaining these materials usually requires breakage of the cell to release the biomaterials. In the past, this breakage has been achieved by varying methods including sonication, grinding with abrasive materials at very low temperatures provided by liquid nitrogen, high speed homogenization, and shearing with a Potter homogenizer. These methods present various drawbacks including the need of extensive calibration and control, cumbersome and nonuniform operations, as well as others.

In light of the above discussion, it is evident that there is still a need for improvements in processing and recovering biomaterials. For instance, there is a need for an improved process for generating DNA fragments from DNA samples, and shearing cells to recover materials therein. A highly desirable method for producing subclones would produce random DNA fragments, i.e. shearing would be sequence independent. Further, it should be reproducible at any time and with any DNA. To achieve this, shearing should be reached in a steady-state manner, i.e. shearing to a particular size should not be dependent on the time of application of the shearing agent. Also, the method would allow the generation of DNA fragments in a size range of about 500 to 2000 base pairs. The method should be efficient, and the majority of the DNA treated should be converted into the desired size fragments. Moreover, the method should be applicable to both large and a small quantities of DNA, and, importantly, should be simple to perform while not time consuming. Additionally, for example, there is a need for a highly efficient and convenient process for shearing cells to recover biomaterials therein. Such a process would desirably minimize any damage which occurs to the biomaterials during the shearing operation. The applicants' invention addresses these needs.

SUMMARY OF THE INVENTION

In brief summary, one preferred embodiment of the invention provides an improvement in a process for fragmenting a biomaterial and isolating and recovering a component thereof. In so doing, the preferred process comprises the step of performing said fragmenting by nebulizing a liquid containing the biomaterial.

Another preferred embodiment of this invention relates to a process for fragmenting isolated DNA. In so doing, this process comprises the step of nebulizing liquid containing the DNA, whereby DNA fragments are produced.

Another preferred embodiment involves a process for determining a sequence of a DNA strand, comprising the steps of (i) nebulizing liquid containing the DNA strand to thereby form DNA fragments, and (ii) determining by analysis of the fragments, a sequence of the DNA strand.

Still another preferred embodiment of the invention relates to an improvement to a nebulization device having a liquid input and a liquid output. Pursuant to the invention, the device also comprises means for returning liquid from the output back to the input.

Without limiting the invention, it is believed that in the process of droplet formation, DNA or other biomaterial, suspended in the liquid being nebulized, is forcefully distributed to the surface of the forming bubble in a transient flow between the liquid surface and the droplet. It is believed that this flow exerts sufficient shearing forces on the suspended DNA molecules or other biomaterial to mechanically break them into small fragments. Further, it is believed that nebulization of DNA or other shearable polymers results in the breakage of each molecule approximately in half in the repeated process of bubble formation, until the molecule reaches a small enough size that the forces applied are not sufficient to break it any further. As a result, the DNA or other polymer molecules are sheared in a steady-state manner, and the final size of the broken molecules will depend only on the extent of the force applied. Moreover, the smallest shear stress that can break molecules decreases with increasing molecular weight of the DNA, resulting in very quick shearing of a large molecules thereby adding to the effectiveness of the procedure. The extent of the shearing force created should theoretically be formally proportional to the pressure drop described by the equation of liquid capillary flow. Accordingly, this force will be directly proportional to the gas pressure applied and the viscosity of the liquid, and inversely proportional to the size of the droplets. Consequently, the smaller the droplets, the higher viscosity and greater gas pressure applied, the larger the shearing forces that will be exerted on the molecules or other biomaterials.

One object of this invention is to provide improved processes for processing and recovering biomaterials, including for example improved processes for fragmenting and for sequencing DNA, improved processes for shearing cells and recovering biomaterials therein, and improved processes for shearing biopolymers such as starch.

Another object of the invention is to provide a device for repeated nebulization of liquid, which can advantageously be used in the applicants' preferred processes. Additional objects, as well as advantages of the invention, will become apparent upon reviewing the following description and the appended claims.

BRIEF DESCRIPTION OF THE FIGURES

FIG. 10 is a graph comparing supernatent Absorbance (in OD units) at 260, 280 and 652 nanometers for 1 and 6 stroke Potter homogenizer treatments and a 1 minute nebulizer treatment of soybean culture cell samples.

DESCRIPTION OF THE PREFERRED EMBODIMENTS

Figure 1:
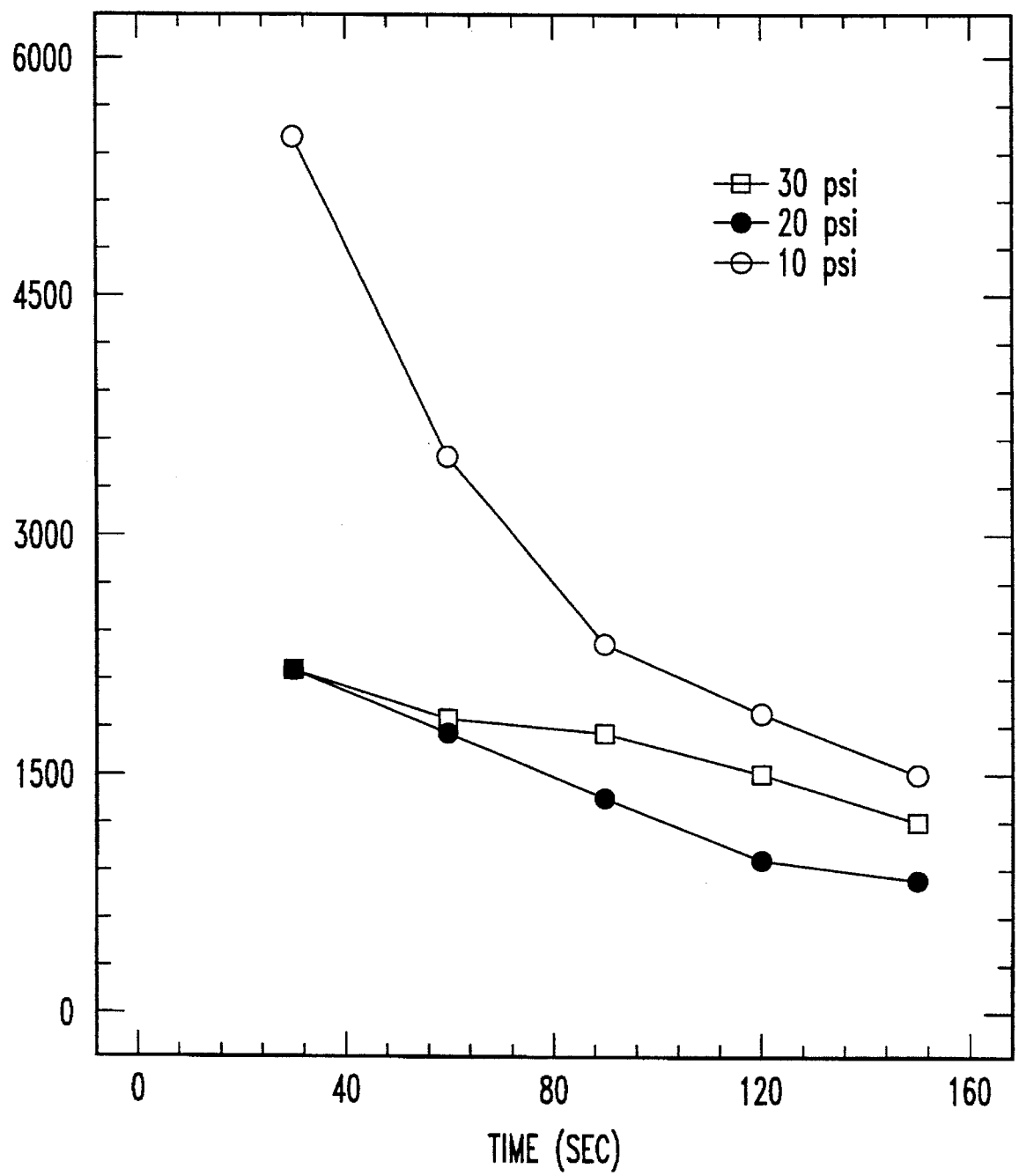
FIG. 1 is a graph of average DNA size versus time at varying pressures during nebulization.

For the purposes of promoting an understanding of the principles of the invention, reference will now be made to certain embodiments and specific language will be used to describe the same. It will nevertheless be understood that no limitation of the scope of the invention is thereby intended, such alterations, modifications and further applications of the principles of the invention being contemplated as would normally occur to one skilled in the art to which the invention relates.

As stated above, one preferred embodiment of the invention relates to an improvement in a process for fragmenting a biomaterial (i.e. modified or unmodified biologically-occurring material) and isolating and recovering a component thereof. Such biomaterials include, for example, cells or cell subfractions, e.g. proteins, shearable long polymers such as DNA and starch polymers, chromosomes, organelles such as nuclei, chloroplasts, mitochondria, etc.

The shearable material to be fragmented is introduced into a suitable liquid, typically an aqueous medium, and this liquid is then nebulized so as to shear the biomaterial. Preferably, the liquid is nebulized a plurality of times by either batch collection and renebulization or a continuous nebulization and recirculation process.

As indicated, a preferred mode and embodiment of the invention relates to a process for fragmenting isolated DNA, which comprises the step of nebulizing a liquid containing the DNA. The applicants' work has demonstrated that producing DNA fragments using nebulization shearing provides many important advantages heretofore desired to a great extent in this field. For example, this process has proven to give highly random fragmentation of DNA. The process is easily reproducible, and achieves shearing in a steady state manner. In fact, using the inventive process, it has to date been possible to generate DNA fragments of a selected size, in the range of about 500 base pairs ("bp") to about 2000 bp, with efficiencies above 30%, ranging as high as 50% and even 70% or more in the applicants' work thus far. Further, this size range can be extended below 500 bp size by increasing gas pressure, by increasing viscosity of the liquid, and/or by other means, as further discussed below. Moreover, in fragmenting DNA and in other shearing or breaking processes, the nebulization process does not generate significant heat as does sonication, but rather has an inherent or "built-in" cooling mechanism due to the evaporation of mist droplets.

The term "nebulization" is well known in the art to include reducing liquid to a fine spray. Preferably, by such nebulization small liquid droplets of uniform size are produced from a larger body of liquid in a controlled manner. This nebulization can be achieved by any suitable means therefor, including by using many nebulizers known and marketed today. For example, representative processes were conducted by applicant using an AEROMIST pneumatic nebulizer available from Inhalation Plastic, Inc. of Niles, Ill. The opening of the AEROMIST nebulizer was partially closed with a cone-shape pressure valve, and the resulting mist was recirculated back to the reservoir by virtue of this valve to avoid a large loss of liquid. Recovery of the liquid in this procedure was approximately 80 to 90%. As is well known, any suitable gas can be used to apply pressure during the nebulization, with preferred gases to date being those which are chemically inert to the nucleic acid. In this regard, from applicants' work to date, a preferred gas is nitrogen, although other inert, gases such as argon or helium can be used to high advantage. In the work using nitrogen gas, a standard nitrogen tank gas regulator was used to control the gas pressure.

As to the isolated DNA starting material, such DNA from any source is acceptable for the applicants' invention. As used herein, the term "isolated DNA" is meant to include DNA which is free from any significant amounts of other materials which would significantly complicate the recovery of the DNA fragments in the preferred processes. Such DNA in purified form is commonly available from commercial sources or can be prepared using procedures well known and used in the art. Representative DNA's in the applicants' work have included lambda and puc 19 DNA, *Chlamydomonas reinhardtii* chloroplast DNA purified from the WT 137C strain. Further illustrative DNA's have been high molecular weight chromosomal DNA of *E. coli*. However, as stated above, such DNA from any source is suitable as will be appreciated by those practiced in this field.

Similarly, any suitable liquid in which the DNA can be safely suspended without significant degradation is suitable for the invention. Typically, however, the liquid will be water with or without other additives.

In other aspects of the present invention, controlled DNA shearing has been achieved by varying the the gas pressure and viscosity of the media in the nebulization step. For example, suitable agents have been included in the liquid to increase its viscosity, which, as discussed in more detail in Examples 6 and 7 below, has a dramatic effect on the size of the DNA fragments obtained as well as the efficiency of the shearing process. In this regard, preferred viscosity-increasing agents for aqueous mediums have included suitable alcohols such as ethylenesglycol and glycerol, and suitable sugars such as sucrose. Additionally, the size of the DNA fragments resultant of the inventive process has been reliably controlled by regulation of pressure, since the DNA fragment size is inversely proportional to the gas pressure used in the nebulization step.

In another aspect, the DNA fragment size can by increased by nebulizations which take advantage of the self-protection phenomenon by using starting DNA concentrations higher than about 50 μg/ml DNA (see Example 4 and FIG. 2). Additionally, one can obtain similar results by including with the starting DNA another suitable polymer, such as starch, to afford DNA protection and thereby obtain larger DNA fragments.

After the nebulization step, the DNA fragments are recovered by a suitable method such as precipitation with ethanol. Additionally, as further discussed in Example 8 below, the fragments can be conventionally treated and cloned, sequenced, and the data entered appropriately into a data base. By analysis of data thus obtained, a sequence of larger DNA strands from which the fragments are derived can be obtained.

As indicated, living cells represent another biomaterial which those practiced in this area commonly break to recover components thereof. These cells include both plant and animal cells, and procaryotic cells. In accordance with the invention, the cells are suspended in a suitable medium such as buffered water. This medium is then nebulized so as to break or shear the cells and thus release components or cell subfractions within, e.g. chromosomes, DNA, proteins, organelles such as nuclei, mitochondria, chloroplasts, etc. For example, the applicants' have demonstrated breakage of *Chlamydomonas reinhardtii* and Chlorella (green algae), Asparagus, soybean cells, and yeast cells and identified release of nucleic acid and protein subfractions which can then be isolated and recovered by standard techniques. As another example, the applicants have also nebulized *E. coli* cells under suitable (mild) conditions so as to release only plasmid DNA into the medium. This permits quick and efficient isolation of the plasmid DNA. The applicants have also nebulized *C. reinhardtii* cells suitably to release only proteins (e.g. enzymes) from periplasmic compartments of the cells. Enzyme so released has proven to retain its enzymatic activity, and thus this approach provides an effective and selective recovery of proteins bioengineered to be deposited into the periplasmic spaces of cells. Further, applicants have released chloroplast carbonic anhydrase from *C. reinhardtii* using sonication, Yeda press and by their inventive nebulization process, and have compared the activity of the recovered enzymes. The enzyme activity was nearly identical for the three methods, again demonstrating the ability to recover proteins intact.

In general, when shearing cells, the nebulization will be suitably controlled to avoid any substantial damage to the subfraction or component to be isolated and recovered. In this regard, the nebulization pressure employed will vary in accordance with the particular type of cells being sheared and the viscosity of the supporting liquid medium.

As indicated above, another preferred embodiment of the invention relates to an improvement to a device for nebulizing liquid which device has an input and an output. In accordance with the invention, the device also comprises means for returning nebulized liquid from the output of the nebulizer back to the input of the nebulizer.

Using the commercial nebulizers available at the present time, significant limits are placed on the efficiency and efficacy of nebulization shearing of DNA. For example, these include difficulties in capturing and recirculating the nebulized liquid again through the nebulizer, since the known devices have no means to accomplish this. Additionally, DNA fragment size distribution and process efficiency can be varied not only by changing liquid viscosity or gas pressure, but also by other means which vary the size of the droplets obtained in the nebulization. Particularly, known devices also have a capillary channel feeding the liquid to the nebulization zone, as well as a barrier, usually hemispherical in shape, positioned a distance from the liquid output and which breaks droplets exiting from the output into even smaller droplets. The size of the capillary channel and the shape and relative positioning of the barrier also effect the size of the droplets from nebulization. None of the known devices, however, have any means for varying the size of the capillary channel, for interchanging one barrier for another of differing shape, or for varying the distance of the barrier from the output. The applicants' preferred inventive devices incorporate these further features by which the size of the droplets can be varied and accordingly the efficiency and efficacy of the DNA shearing process can be controlled.

Figure 7A:
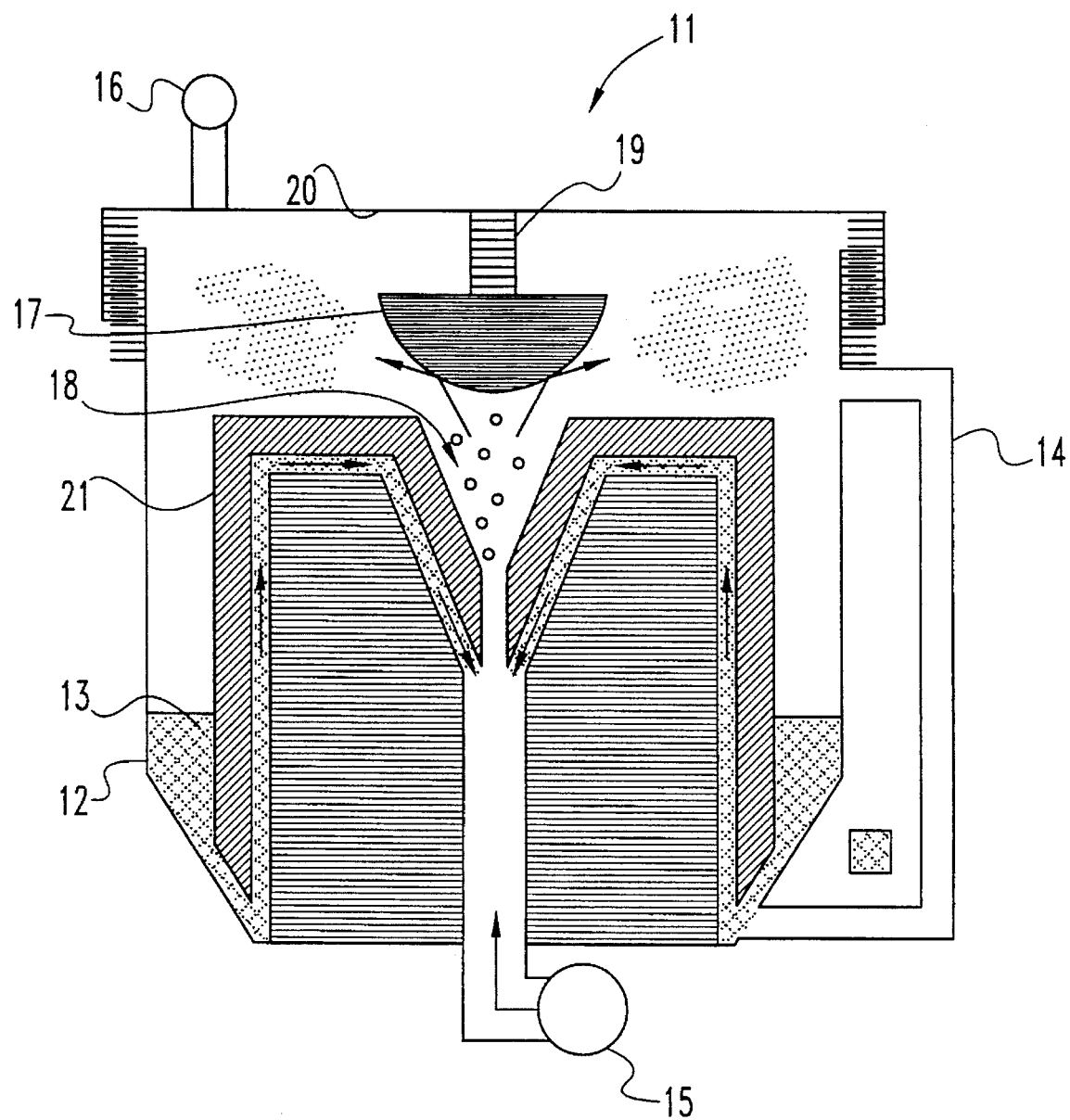
FIG. 7A is a schematic representation of an improved nebulizer device in accordance with the invention.

In particular, shown in FIG. 7A is a schematic of an improved nebulizer 11 incorporating these inventive features by which the size of sheared DNA and efficiency of nebulization processes can be improved. In particular, the nebulization device 11 can be conventional except for the following features. First, the reservoir 12 of the nebulizer 11 is preferably conical in shape, which permits nebulization of very small volumes of liquid 13. Further, the reservoir 12 is preferably hermetically sealed and has a return tube 14 to recirculate nebulized mist. This makes it possible to efficiently nebulize the liquid 13 containing the DNA for extended periods of time. Additionally, the preferred nebulizer 11 of this invention has a gas pressure valve 15 and a pressure relief valve 16 which are co-adjustable. These provisions enable maintaining constant gas pressure inside the reservoir 12.

The preferred nebulizer device 11 also includes means for adjusting the distance between the barrier 17 and the output nozzle 18, which means can be provided by threading the support 19 for the barrier 17 so that it can be screwed into and out of the opposing surface 20. Of course, this function can be accomplished by any other suitable means. Additionally, the preferred device 11 has means for exchanging the barrier 17 for another barrier, such as a barrier of differing size or shape. This may be accomplished in the preferred device by completely threading the support 19 out of the surface 20 and threading in a new support and associated barrier. Alternatively, the support can be permanently attached to the surface 20, and the barrier can be adjustably and removably attached to the outward end of the support, as by threads or any other suitable means. These aspects permit the choice of optimal distance and shape of the barrier for various shearing applications. Further, the preferred nebulizer device 11 has means for adjusting the diameter of the capillary channel feeding liquid into the nebulizing zone. For instance, this can be accomplished by including a vertically adjustable cup 21 in the device 11. Further control of the size of the droplets producible by the nebulizer is thus provided. As stated above, the nebulizer may be conventional in structure other than the preferred features mentioned herein.

Figure 7B:
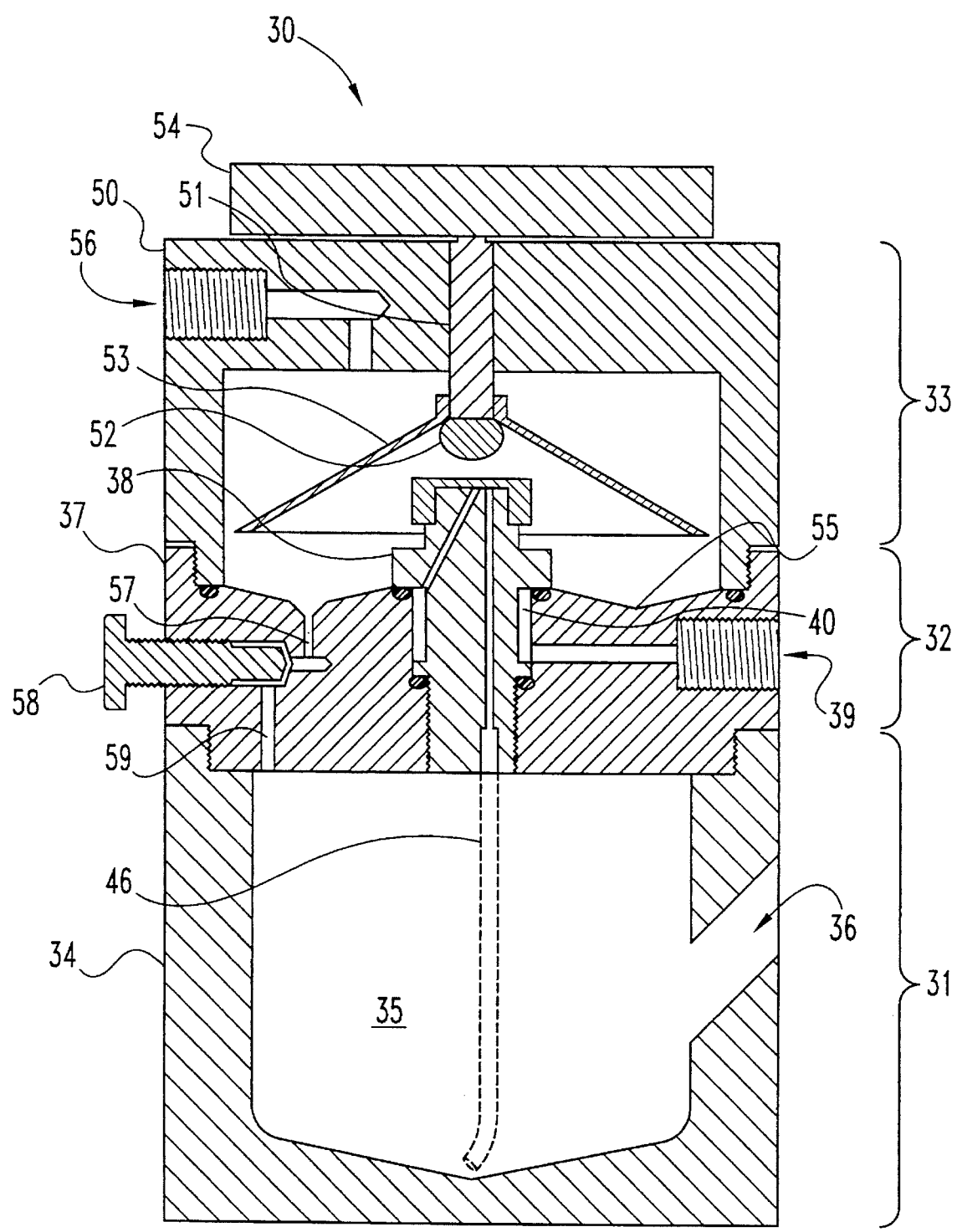
FIG. 7B is a cross-sectional view of a nebulizer device in accordance with the invention.

Referring now to FIG. 7B, shown is is a cross sectional view of a nebulizer device 30 incorporating some of the features of the invention. In particular, nebulizer device 30 is generally cylindrical in shape, and generally includes three chambers, those being sample chamber 31, gas pressure chamber 32, and nebulization chamber 33. Chambers 31–33 are suitably connected and sealed to each other, for instance by cooperating threads and the provision of compressible washers (shown by solid dots in FIG. 7B) or the like between them.

With continued reference to FIG. 7B, sample chamber 31 serves as a receptacle for the sample to be nebulized. Sample chamber 31 has a body 34, preferably constructed of a suitable plastic or metal, into which a chamber or reservoir 35 for receiving the sample is constructed. Additionally, a sampling port 36 is preferably provided through which samples of nebulized or non-nebulized materials can be withdrawn with an appropriate instrument without the need for disassembling the nebulizer device 30.

Figure 7C:
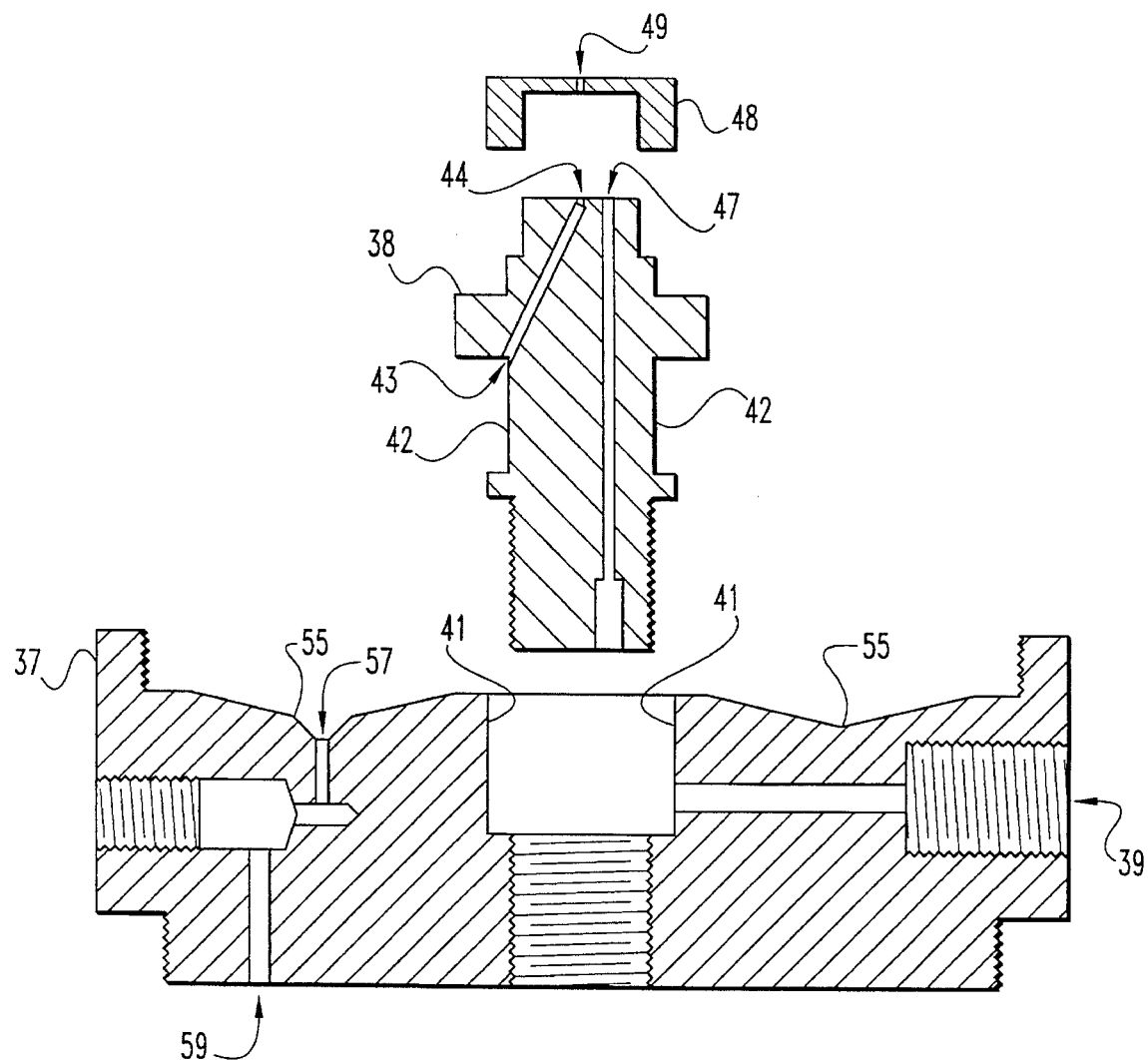
FIG. 7C is an exploded-cross sectional view of central components of the device illustrated in FIG. 7B.

With reference now to FIGS. 7B and 7C together, gas pressure chamber 32 has a body 37, preferably constructed of a suitable metal or plastic, for instance suitably brass. A gas nozzle 38 is secured, preferably threaded, into chamber body 37. Chamber body 37 has a gas intake opening 39. Gas intake opening 39 opens into cylindrical chamber 40 formed between an inner wall 41 (FIG. 7C) of chamber body 37 and an exterior wall 42 of nozzle 38. Channel 43 extends between and connects cylindrical chamber 40 and gas opening 44 at the top of nozzle 38.

Nozzle 38 also has a channel 45 to which a flexible hose or other conduit 46 (shown in dotted lines) can be connected so that the hose 46 extends down into the sample to be nebulized. Channel 45 directs sample to be nebulized to sample opening 47 at the top of nozzle 38. Nozzle 38 is capped by nozzle cap 48 which has a small opening 49 therein. Nozzle cap 48 is secured to the top of nozzle 38, for instance by cooperating threads.

Nebulization chamber 33 includes body 50 having a threaded bore therein into which threaded member 51 is received. A spherical member 52, preferably constructed of a suitable metal, e.g. stainless steel, is provided at the end of threaded member 51. Nebulization chamber 33 also includes a generally conical deflector 53. A dial 54 is attached to the top of threaded member 51, and can be rotated to adjust the distance between spherical member 52 and opening 49 of nozzle cap 48.

With continued reference to FIGS. 7B and 7C, the operation of nebulization device 30 will now be further described. A sample of material to be nebulized is placed into chamber 35, with the hose 46 extending into the sample. A source of pressurized gas is connected to gas intake opening 39. When thereafter pressurized gas is directed through opening 39, it passes into chamber 40, upwardly through channel 43, and out of openings 44 and 49 which are generally aligned. The flow of gas creates a vacuum which pulls sample up through the hose 46 and channel 45, out of sample opening 47, through the narrow space provided at the interface of the top of nozzle 38 and the bottom of nozzle cap 48, and to opening 49 where it is converted to a mist by the gas exiting opening 49. This mist, designated the "primary mist", is directed at and strikes spherical member 52 which provides a nonplanar contacting surface. A finer mist of even smaller droplets, designated the "secondary mist", is thereby created. With the aid of deflector 53, this secondary mist is mostly collected in channel 55 formed by the concaved upper surface of chamber body 37. After participating in the nebulization process, gas escapes through gas opening 56 to the external environment. If desired or necessary, gas opening 56 can be fitted with an aerosol barrier filter or another suitable device for preventing escape of materials other than the gas.

Chamber body 37 also has a channel 57 provided with a valve member 58. The valve member 58 can operate to selectively and reversibly provide (e.g. by screwing or unscrewing member 58 into or from body 37) fluid communication between channel 57 and channel 59 to empty nebulized sample back into reservoir or chamber 35. In this manner, sample collected in channel 55 can optionally and selectively be recirculated back into chamber 35 by operating valve member 58. Thus, three types of nebulizing operations can be performed with the device 30. First, sample can be nebulized only once and then removed from device 30 for further processing. Second, batch recycling can be performed by nebulizing a sample while having valve member 58 in the closed position. The nebulized sample is thus allowed to accumulate in channel 55 until the nebulizing procedure is completed. Thereafter, the nebulized sample can be returned to the sample chamber 35 by opening the valve member 58, whereafter the valve 58 can again be closed. Then, the sample can be nebulized again, and the operation repeated to provide batch operation of the device 30. Third, device 30 can be operated in a continuous fashion, for instance by leaving the valve member 58 open during a nebulization operation. The nebulized material may then be recirculated into chamber 35 for renebulization, or diverted to a separate collection vessel to provide operation of device 30 in a single pass continuous mode.

To promote a further appreciation and understanding to the principals and advantages of the invention, the following illustrative Examples are provided. The lambda and puc 19 DNA used in the Examples were purchased from U.S. Biochemicals Company of Cleveland Ohio. *Chlamydomonas reinhardtii* DNA was purified from the WT 137C strain. Chloroplast DNA was separated from the nuclear DNA by centrifugation through two successive $CsCl_2$ gradients. High molecular weight chromosomal DNA of *E. coli* was prepared from strain C600 essentially as described by T. Manniatis et al., *Molecular Cloning Laboratory Manual*, Cold Spring Harbor Laboratory (1982). T4 DNA ligase, Klenow fragment and T4 DNA polymerase were purchased from Boehringer-Manniheim Co. The 1Kb DNA ladder molecular size standard was purchased from BRL.

In general, DNA was suspended in 2 ml of TE buffer and subjected to nebulization by applying gas pressure using various conditions as described in the Examples. When lambda DNA was used for experiments, it was heated for 10 minutes at 60 degrees Celcius prior to nebulization. After nebulization, DNA samples were electrophoresed on a standard 1.2% agarose gel using TAE electrophoresis buffer. The gels were stained with ethidium bromide and photographed. Negatives were subsequently scanned using a QuickScan Density Scanner with area integrator. The average size of DNA fragment was estimated using a computer program that compares the position of the main DNA peak with the distance traveled by a DNA standard in the same gel. The percent of DNA present in the area of the gel ±200 bp away from the position of the main peak was calculated by dividing the area of the scan enclosed in these boundaries by the total area of DNA and multiplying by 100. The ends of DNA fragments were repaired to generate blunt ends using T4 DNA polymerase together with Klenow fragment (as described by F. M. Auzibel et al., *Current Protocols In Molecular Biology*, John Wiliey and Sons (1989). The fragments were subsequently ligated with T4 ligase using conditions suggested by the manufacturer for blunt end ligation. The extent of ligation was determined using agarose gel electrophoresis as described by the manufacturer of ligase.

EXAMPLE 1

The Effect of Varying Gas Pressure on DNA Breakage

Lambda phage DNA or *E. coli* DNA were nebulized using the device and procedure described above. FIG. 1 presents the results of one such experiment using *E. coli* DNA. The DNA was nebulized for the time indicated using three different gas pressures. Samples were withdrawn, and DNA fragments were separated according to size using agarose gel electrophoresis. The average size of the resulting DNA fragments was measured as described above. The results show that : (a) the nebulization process can break large DNA molecules very efficiently, within 30 second the majority of DNA molecules were sheared to at least 6000 bp fragments, even at very low gas pressure; (b) nebulization of DNA is a steady-state process, very little additional shearing occurred after 90 seconds of nebulization, regardless of the gas pressure; and, (c) the average size of DNA fragments at steady-state depends on the gas pressure applied.

EXAMPLE 2

Example 1 was repeated, except Lambda DNA was used rather than *E coli*. Quantitatively, the same results were obtained. Because the original size of these DNAs are very different this result tends to indicate that the average fragment size of DNA obtained at steady-state is independent of the initial DNA size.

EXAMPLE 3

Effect of Nebulization on Supercoiled DNA

To investigate the effect of nebulization on supercoiled DNA, a small amount of supercoiled Puc 19 DNA was added to the nebulization mixture containing high molecular weight DNA of *E. coli*. Because of the shape and size of these supercoiled molecules, the supercoiled plasmid DNA should be resistant to the nebulization process. As expected, electrophoresis indicated that neither supercoiled monomer, nor supercoiled dimer DNA was sheared in the process of nebulization.

EXAMPLE 4

The Effect of Varying DNA Concentration on DNA Breakage

Figure 2:
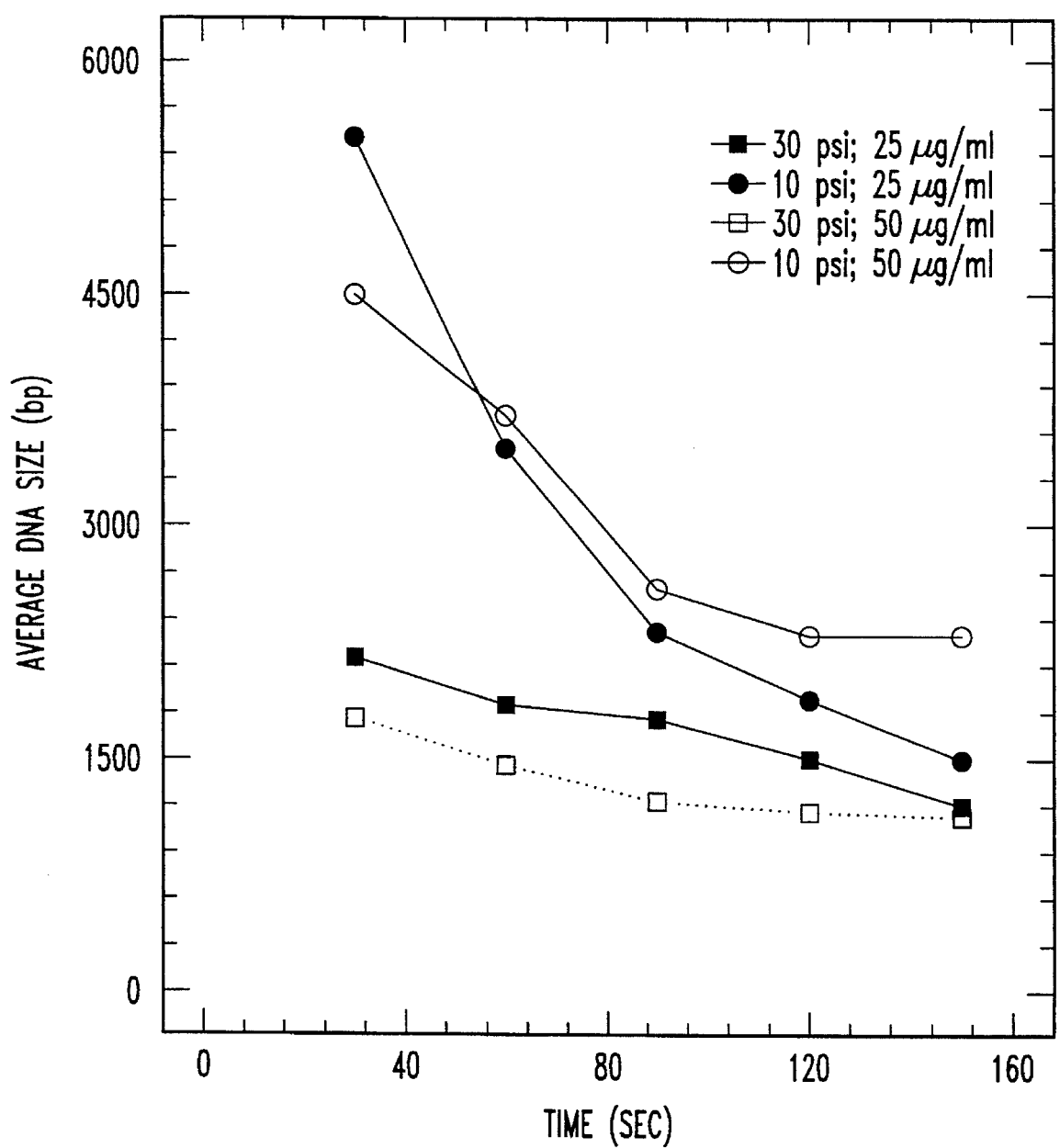
FIG. 2 is a graph of average DNA size versus time at varying pressures and DNA concentrations during nebulization.

The effect of DNA concentration on breakage was investigated in the range of DNA concentrations from 2 µg/ml to 50 µg/ml. The results show that initial DNA concentration has very little effect on the extent and kinetics of DNA shearing. FIGS. 2 presents typical results of such experiments with chloroplast DNA of *Chlamydomonas reinhardtii*. The DNA in this experiment was nebulized using gas pressure of either 10 or 30 psi, and two DNA concentrations, 25 µg/ml or 50 µg/ml. The average size of the fragments at steady-state was nearly identical for both DNA concentrations at high gas pressure and at low gas pressure and low DNA concentration. The average size of DNA fragments at a steady-state was higher when a high concentration of DNA and low pressure was used (FIG. 2, open circles). This is because the resistance of DNA to shear increases at very high DNA concentrations owing to the phenomenon of "self-protection". The experiment also tends to indicate that the self-protection phenomenon is not a factor in the nebulization process when the DNA concentration is under about 25 µg/ml.

EXAMPLE 5

Efficiency of DNA Shearing

Figure 3:
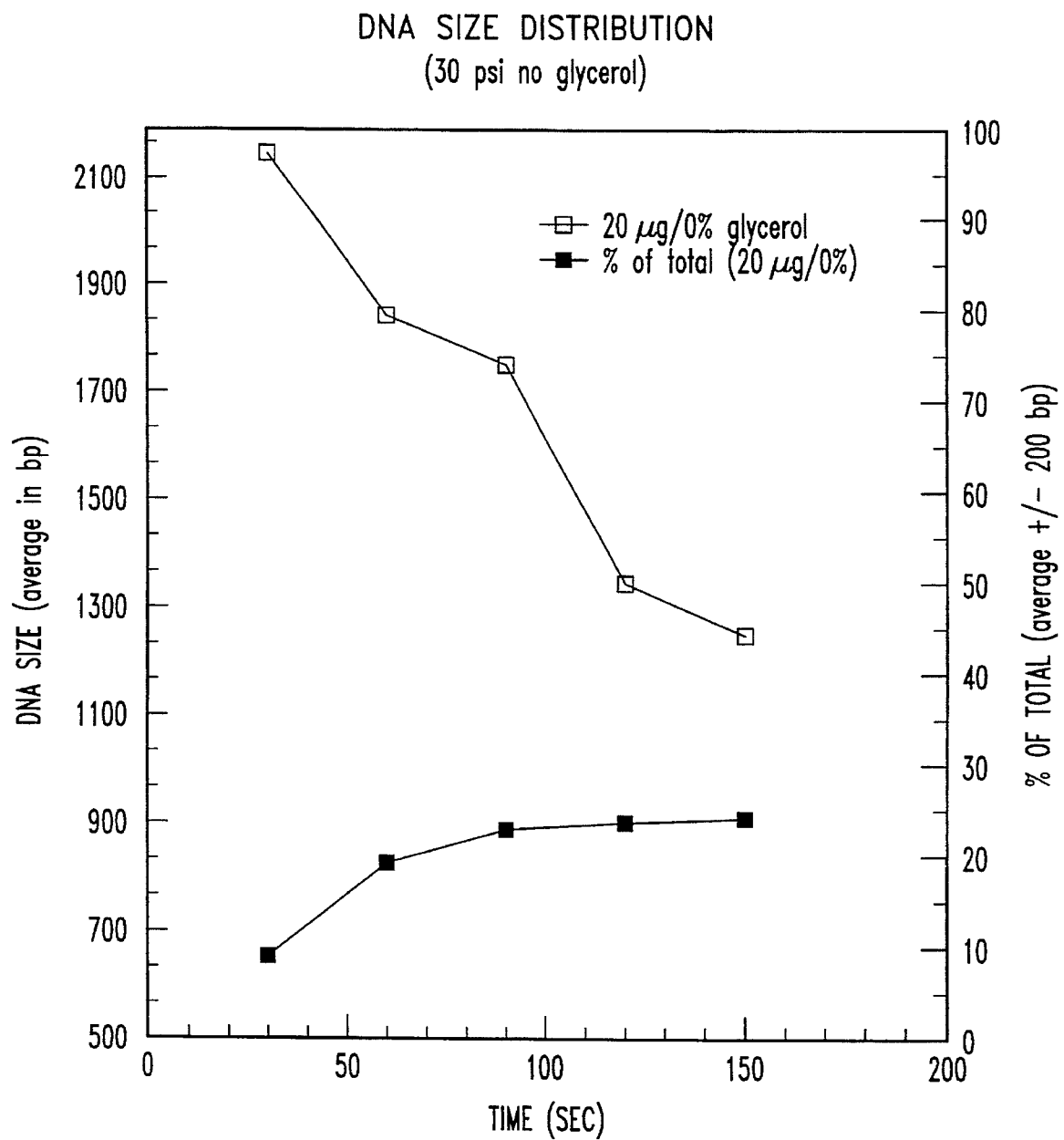
FIG. 3 is a graph of average DNA size versus time using varying concentrations of glycerol during nebulization.

An important parameter of the DNA shearing process is its efficiency, defined as the percent of DNA fragments present in an average size class. If the shearing process is efficient, the size distribution of DNA fragments will be narrow and most of the DNA molecules will be of a similar size. FIG. 3 presents the results of size distribution analysis of lambda. DNA, sheared at a pressure of 30 psi, and a concentration of 20 µg/ml. The size distribution was measured as the percent of DNA fragments present in the size range of ±200bp away from average fragments size. As time of nebulization increases, the average fragment size decreases from 2200 bp (30 seconds) to approximately 1250 bp at time of 150seconds (FIG. 3, open squares). Simultaneously, the efficiency of DNA shearing increases from about 8% at 30 seconds to 25% at a steady-state, reached approximately after 100 seconds. This behavior illustrates the steady state-nature of DNA fragmentation during liquid nebulization, it also indicates that the shearing forces generated under the conditions of the experiment, when the viscosity of the liquid is low, are not sufficient to shear DNA molecules below about 1250 bp. By increasing the shearing force, the size of DNA fragments at steady state may be decreased, and the efficiency of DNA fragmentation improved.

EXAMPLE 6

The Effect of Varying Viscosity on DNA Breakage

It is possible to increase the shearing force exerted on DNA molecules during nebulization, not only by changing the gas pressure, but also by increasing viscosity of the liquid. Experimentally, this can be done by the addition of varying amounts of a viscous water soluble liquid, such as glycerol, to the nebulization mixture. In experiments, the concentration of glycerol was varied from 0% to 25% while using gas pressures ranging from 10 psi to 30 psi. *E. coli* and lambda DNA's were again used in these experiments at a concentration of 25 µg/ml. The results with both DNAs were quantitatively essentially the same.

Figure 4:
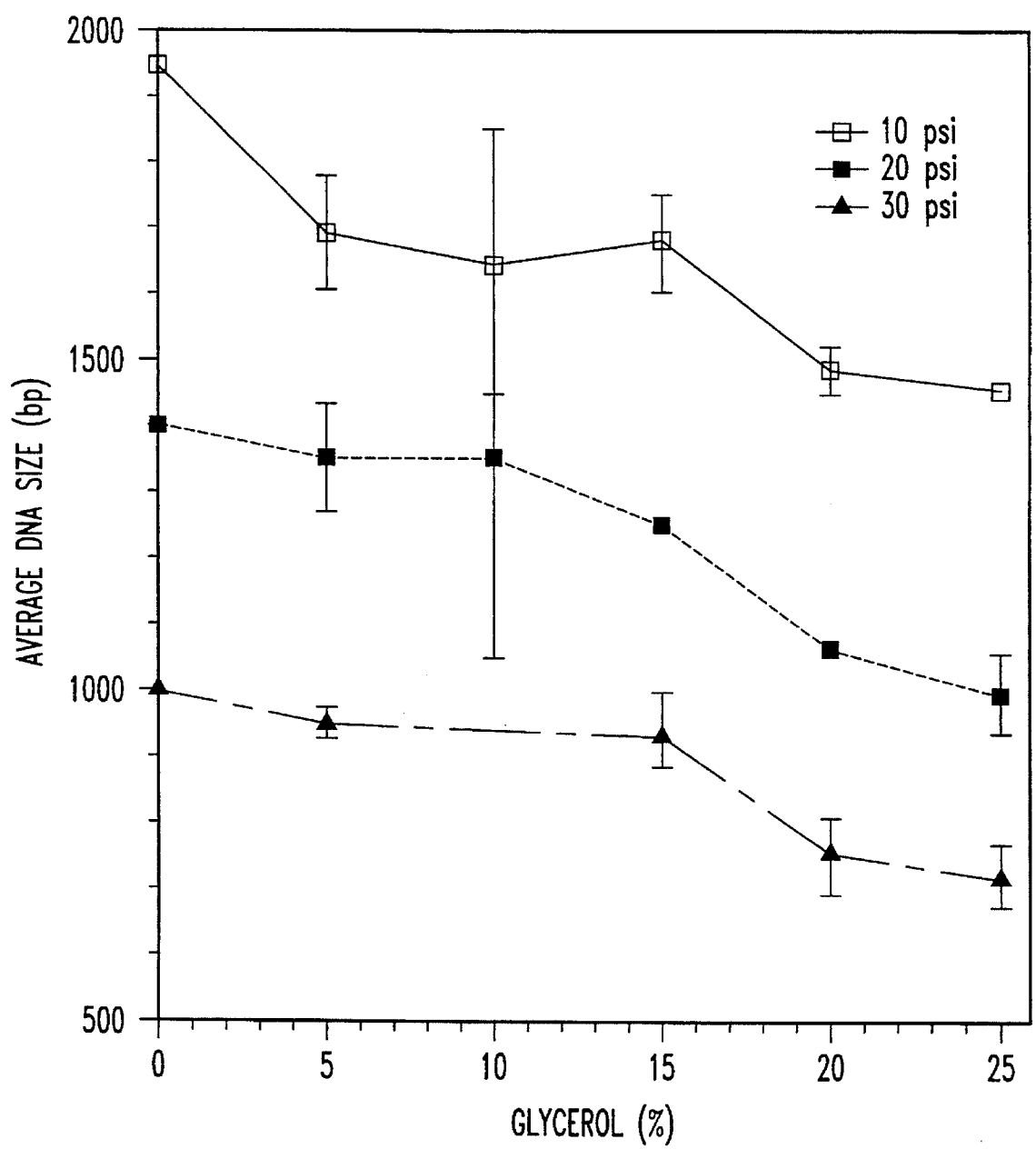
FIG. 4 is a graph of average DNA size versus percent glycerol at varied pressures during nebulization.

The effect of glycerol concentration on the average fragment size of DNA (25 µg/ml) after 120 seconds of nebulization using 10, 20, or 30 psi gas pressures can be seen in FIG. 4. For 30 psi gas pressure the size of DNA fragments changed from approximately 1000 bp when glycerol was not present to about 600 bp at a glycerol concentration of 25%. The average fragment size of DNA did not decrease substantially at glycerol concentration higher than 30% (data not shown). Thus, the minimal size of DNA fragments that one can get in the presence of glycerol at the pressures used is approximately 600 bp. To decrease the size of DNA fragments further one can increase the gas pressure.

Figure 5:
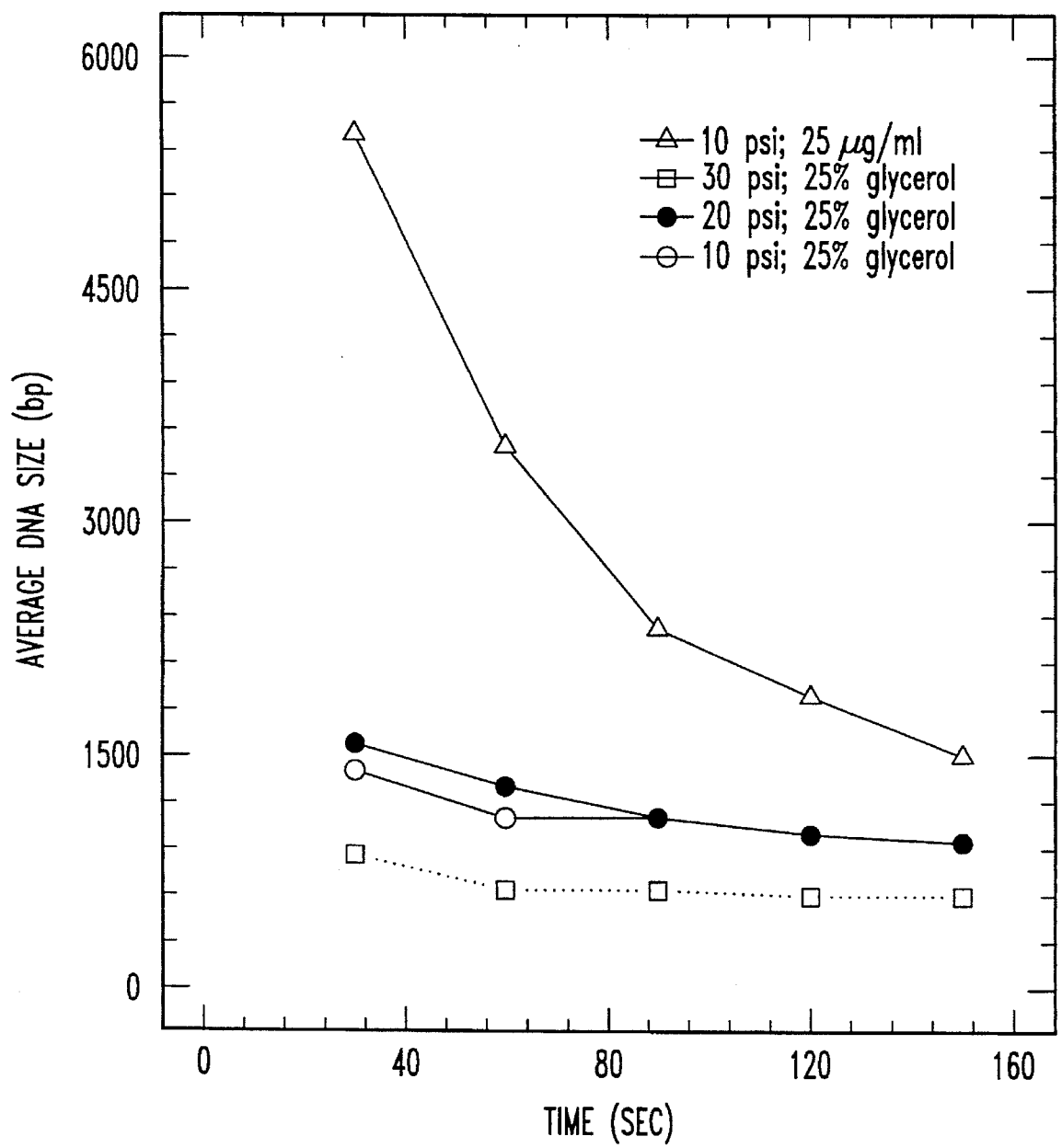
FIG. 5 is a graph of average DNA size versus time for DNA preparations of 25 µg/ml and 25% glycerol at varying pressures during nebulization.

FIG. 5 presents an example of experimental results carried out with *E. coli* DNA to obtain data presented in FIG. 4. FIG. 5 includes, for comparison, data obtained previously, when DNA of *E. coli* was nebulized in the absence of glycerol at a gas pressure of 10 psi. The results indicate that increasing viscosity has a dramatic effect on the extent of DNA shearing. For example, the average fragment size of DNA nebulized at 10 psi for 30 seconds was 5500 bp in the absence of glycerol and 1650 bp in the presence of 25% glycerol (See, FIG. 5). Moreover, the average DNA fragment size at steady-state (i.e. after 100 seconds of treatment) was much smaller than that obtained without glycerol. For example, the average fragment size of DNA nebulized at 30 psi without glycerol was 1250 bp (FIG. 1), whereas the average size of DNA fragment was 600 bp when glycerol was present at concentration of 25%.

Increased viscosity of the solution affected also the time at which the steady-state was reached. The average size of DNA fragment did not change very much after about 80 seconds of nebulization (See, FIG. 5).

EXAMPLE 7

Effect of Varying Viscosity on Efficiency

Figure 6:
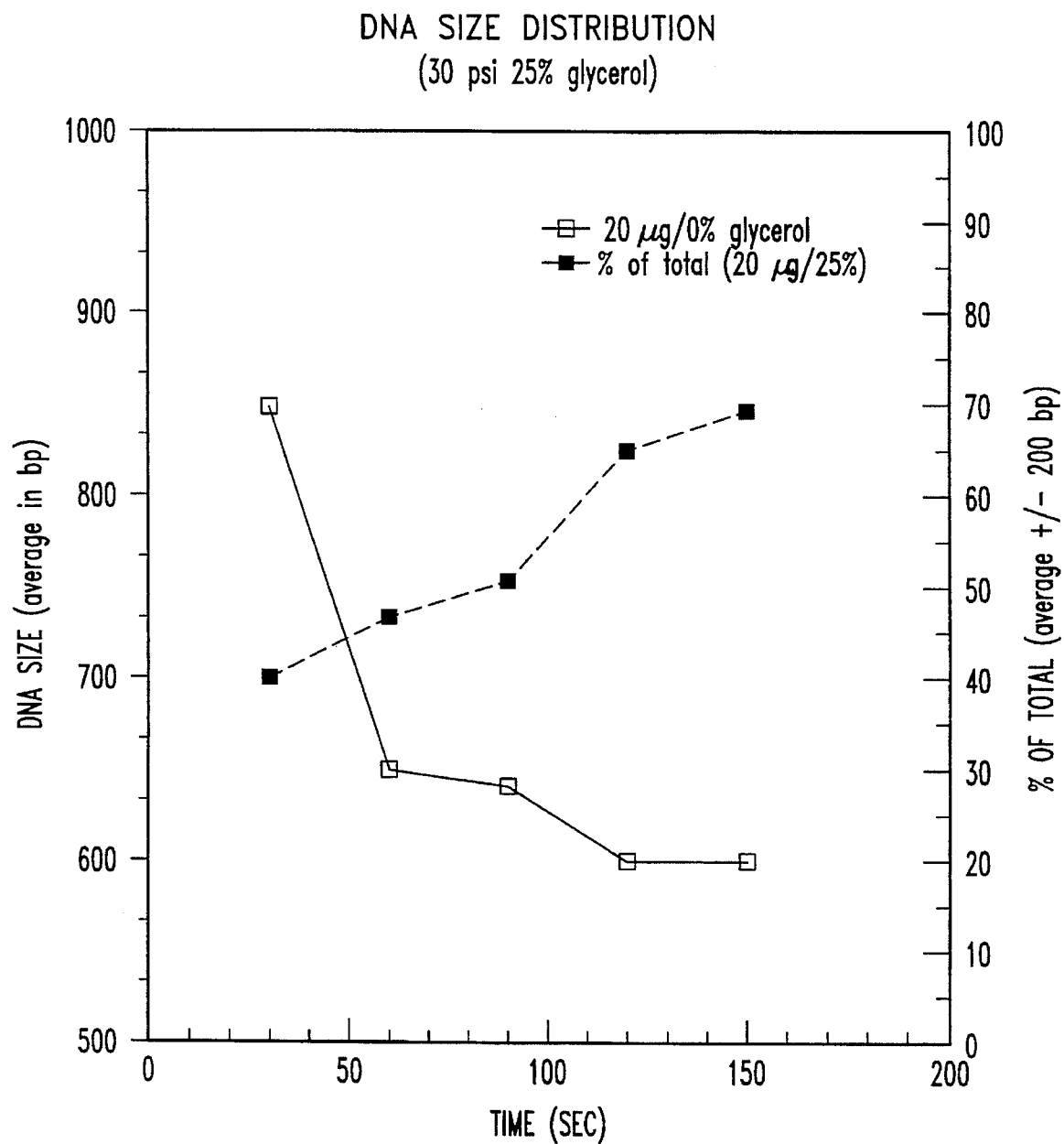
FIG. 6 is a graph of average DNA size and process efficiency versus time using 25% glycerol during nebulization.

Changes in viscosity have a dramatic effect on the efficiency of DNA shearing. FIG. 6 presents the result of the analysis of DNA shearing efficiency at 30 psi and 25% glycerol. The data indicate that, at steady state of the average size, nearly 70% of the molecules are in a size range of 600 bp ±200 bp when the nebulization mixture contains 25% glycerol, as compared to only 20% when glycerol is absent (See, FIG. 3).

Moreover, careful inspection of FIG. 6 suggests that the steady-state level of DNA size distribution had not yet been reached in this experiment because the efficiency of the process increased nearly linearly from 30 seconds to 160 seconds of nebulization shearing. This is in spite of the fact that the average size of DNA fragments had already reached steady-state by this time. This suggests that even after 160 seconds of treatment, not every DNA molecule has "recirculated" through the nebulization channel. Thus, increasing the time of nebulization shearing should further increase the efficiency of the process without any reduction of the average DNA size. With a sufficient length of time, it is possible that efficiencies approaching 100% can be obtained.

EXAMPLE 8

Ligation of DNA Fragments

The fragments generated by nebulization were blunt-end ligated to each other or to blunt-ended puc 19 plasmid, and electrophoresed on the gel. The extent of ligation was determined by a shift of the average size of the DNA fragment to a larger size. Approximately 20% of the fragments could be directly blunt-end ligated to each other or to puc 19. This indicates that about 20% of the molecules contain blunt ends, at least on one end of the molecule. The percent of clonable fragments, as determined by cloning them into blunt-ended puc 19 vector, was about c.a 10%. This indicates that there are few DNA fragments having both ends blunt.

A similar experiment was carried out with DNA fragments in which the ends were repaired with T4 polymerase and Klenow fragment prior the ligation reaction. Consequently 80% of the repaired fragments were capable of blunt-end ligation. Also the efficiency of cloning with these fragments was estimated to be on the order of 80% or more. The ends thus appear to be repairable to a great extent using standard end-repairing procedures. Thus, fragments generated by mechanical shearing during nebulization can serve well for the construction of random sequencing libraries.

EXAMPLE 9

Breakage of *Chlamydomonas reinhardtii* Cells

Figure 8:
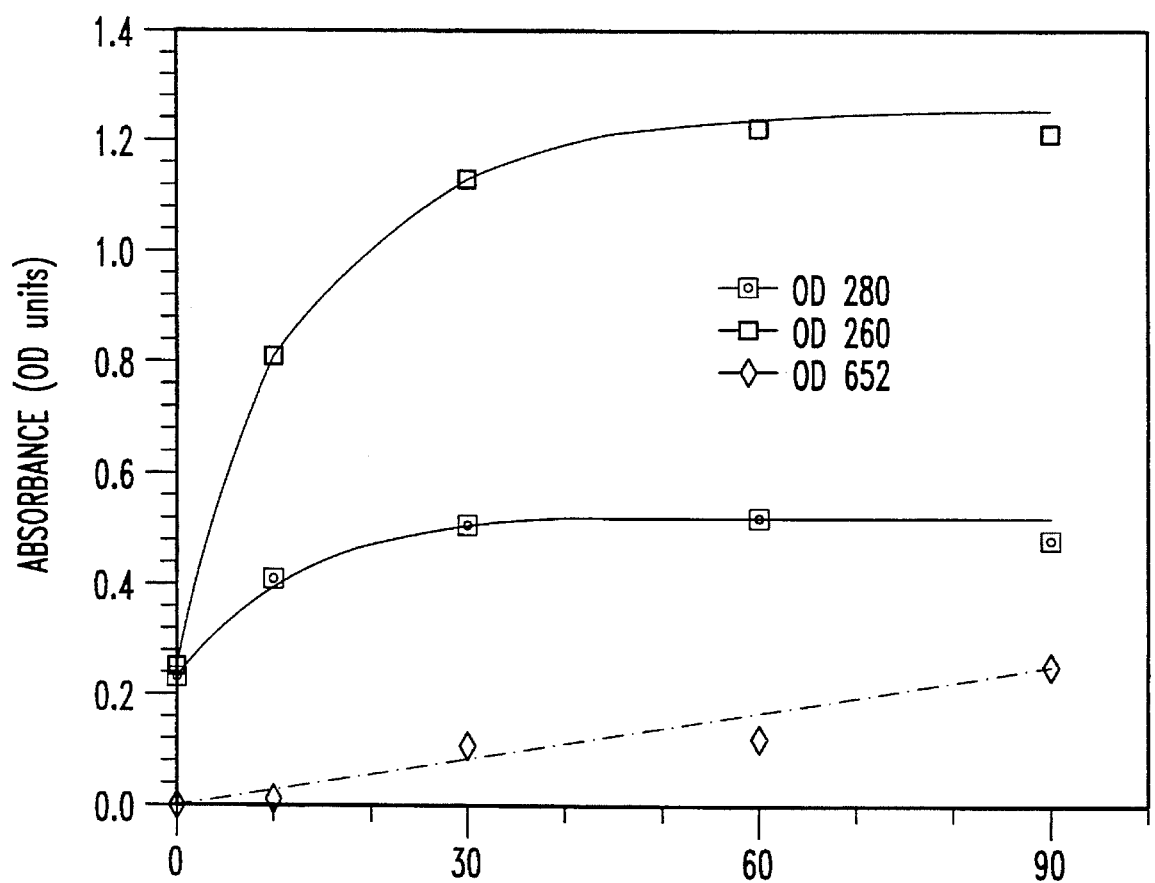
FIG. 8 is a graph of supernatent Absorbance (in optical density "OD" units.) at 260, 280 and 652 nanometers versus nebulization time for samples of *Chlamydomonas reinhardtii* cells.

In this experiment, Chlamydomonas cells were sheared using the nebulization process. Accordingly, two milliliters of these cells (liquid medium=bufferee water) at a concentration of $1 \times 10^8$ were centrifuged to pellet the cells, whereafter the Absorbance of the supernatent at 260 nanometers (nucleic acid Absorbance), 280 nanometers (protein Absorbance) and 652 nanometers (chlorophyll pigment Absorbance) was measured. These measured values constituted the values for intact cells. After this, similar cell-containing mediums were nebulized for 10, 30, 60 and 90 seconds, respectfully, in the previously-described modified AEROMIST nebulizer (10 psi). Subsequently, the mediums were centrifuged, and the Absorbance of their supernatents at 260, 280 and 652 was measured. The level of Absorbance indicated the level of release of the absorbing substance into the medium. The results of this testing are set forth in FIG. 8. They demonstrate that 98% of the cells were broken using this procedure as assessed by cell count and/or absorbance. The nucleic acids and proteins are recovered from the supernatents using standard procedures. In another set of experiments, yeast cells were broken using similar procedures.

EXAMPLE 10

Breakage of Asparagus Leaf Cells

Figure 9:
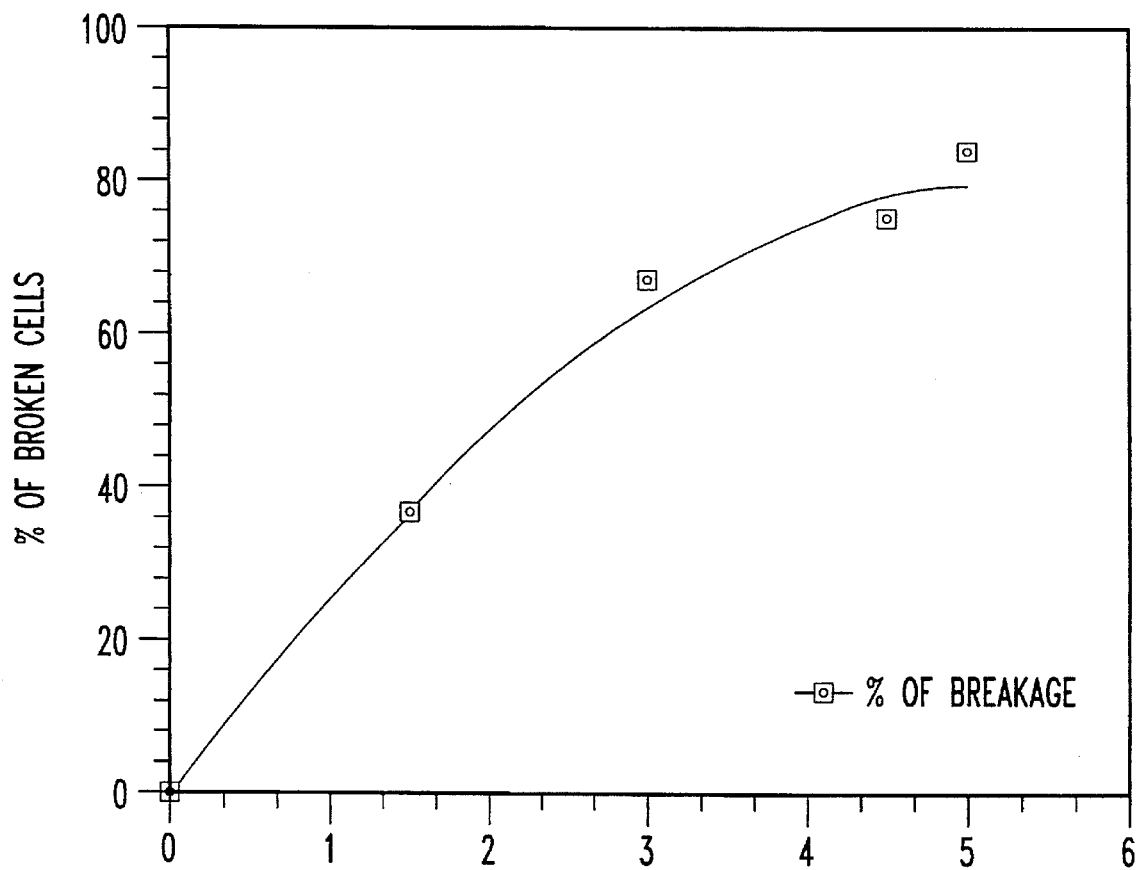
FIG. 9 is a graph of % broken cells versus nebulization time for Asparagus cells.

Two milliliter samples of asparagus leaf cells at a concentration of $6 \times 10^5$ cells/ml (medium=buffered water) were centrifuged in the modified AEROMIST nebulizer (20 psi gas pressure) for 1.5, 3, 4.5 and 5 minutes, respectfully. The percent of cells broken was determined by a cell count in a Clay-Adams counting chamber. The results are set forth in FIG. 9 and demonstrate that greater than 80% of the cells were broken after 5 minutes of nebulization.

EXAMPLE 11

Comparative Cell Breakage in Nebulizer and Potter Homogenizer

In this example, a series of experiments was conducted to compare the breakage of cells by the process of the invention and by a Potter homogenizer. Respective soybean cell cultures were used for these experiments. Similar to Example 9, control values were established for the Absorbance of intact cell medium supernatents at 260, 280 and 652 nanometers. Then, three cell medium samples were treated, two with a Potter homogenizer (1 and 6 strokes, respectively), and one with the modified AEROMIST nebulizer (20 psi, 1 minute). The results are shown in FIG. 10, and demonstrate that the 1 minute nebulizer treatment breaks the cells similarly to the Potter homogenizer after 6 strokes.

EXAMPLE 12

Breakage of Starch Azure

Figure 11:
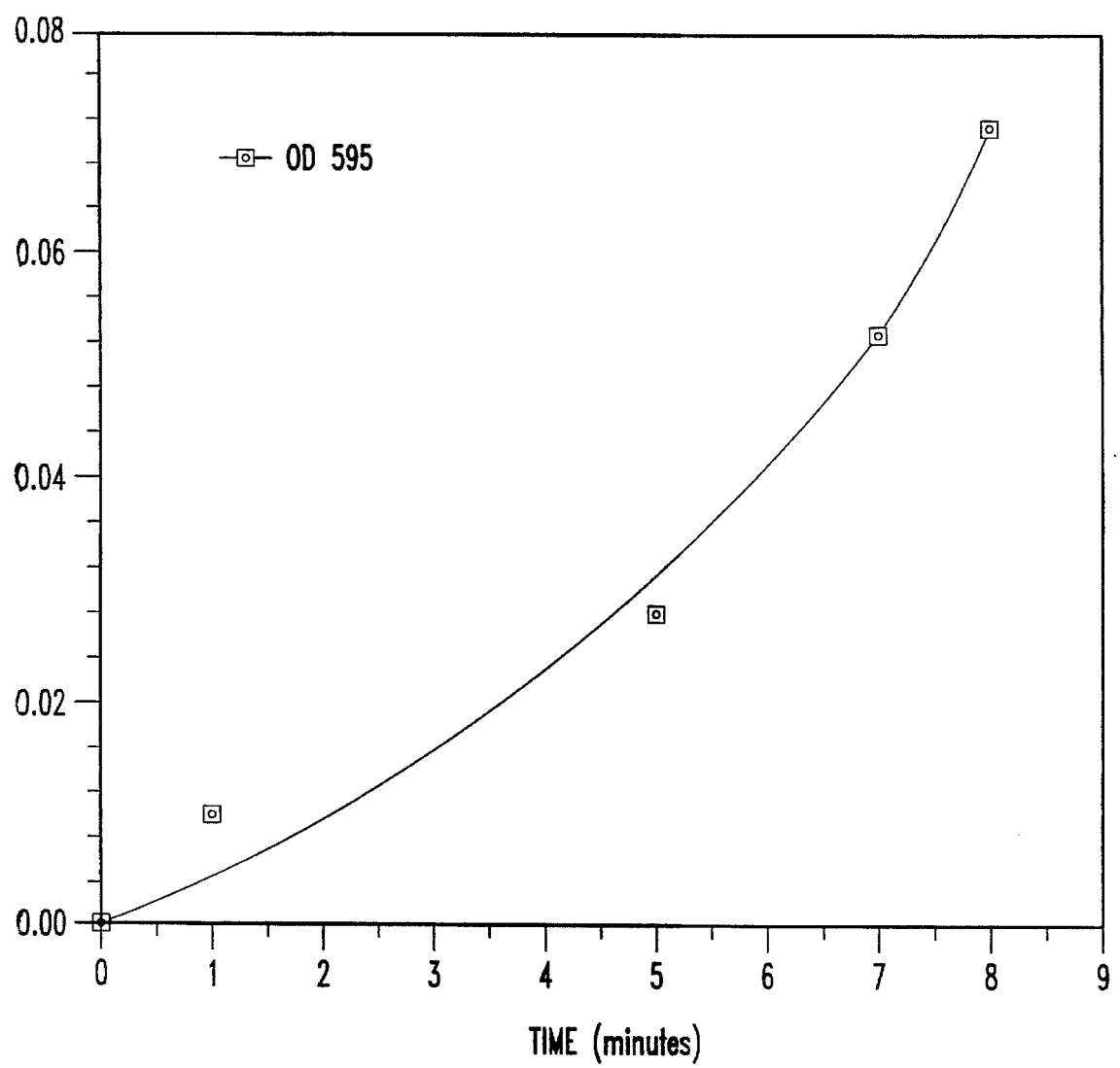
FIG. 11 is a graph of Absorbance (in OD units) at 595 nanometers versus nebulization time for branched polymer starch azure samples.
Figure 12:
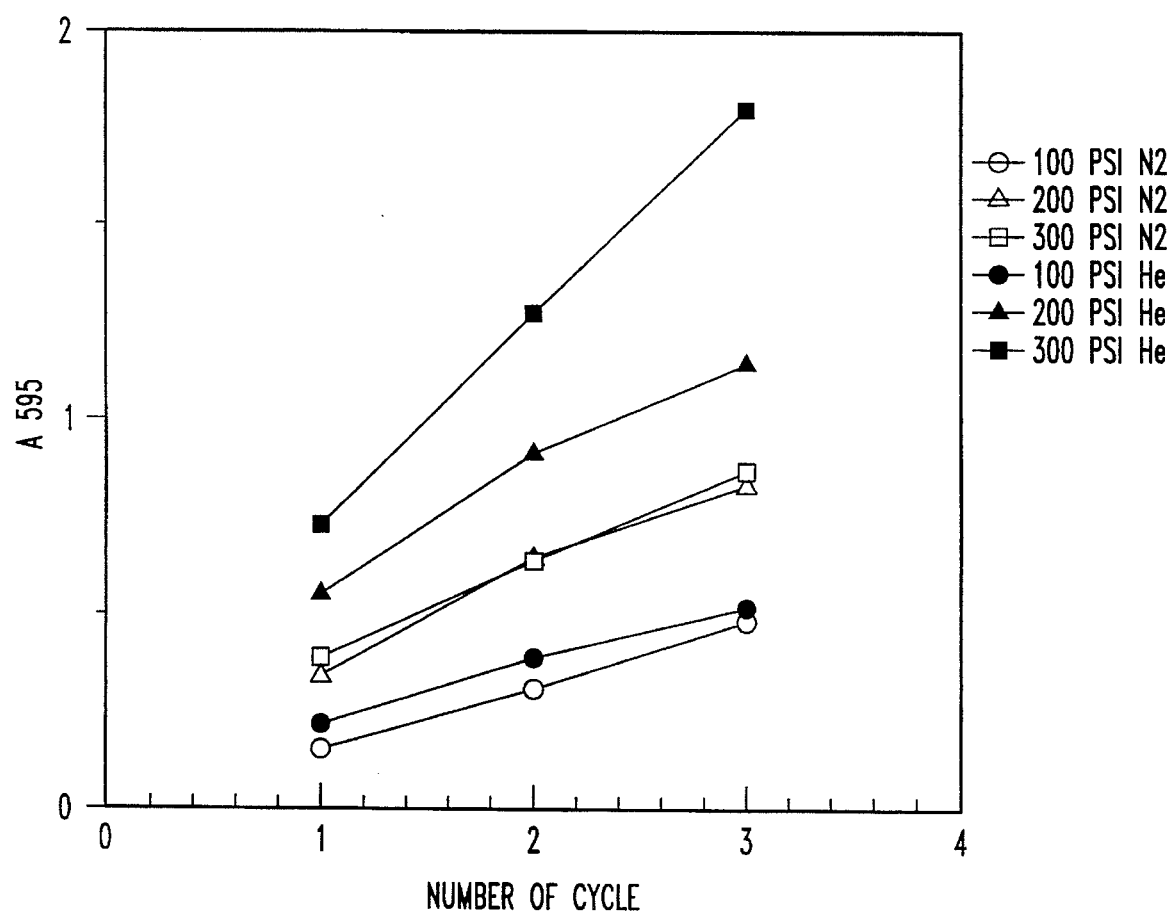
FIG. 12 is a graph of Absorbance of yeast cell supernatants at 595 nanometers versus number of nebulization cycles at varying pressures with Nitrogen and Helium gases.

This example demonstrated the ability of the inventive nebulizer process to break shearable long polymers other than DNA. Accordingly, 2 ml samples of branched polymer starch azure, purchased from Sigma Chemical Co, St. Louis, Mo. (catalog #S-7629) (liquid medium=water, concentration=1 mg/ml) were prepared. These samples were nebulized in the modified AEROMIST nebulizer for 1, 5, 7 and 8 minutes, respectfully, all at 20 psi. Absorbance of the nebulized mediums at 595 nanometers was measured, to indicate the level of breakage. The results, set forth in FIG. 11, demonstrate that this process is highly effective for breaking not only a linear polymer such as DNA but also branched polymers such as starch and other branched polymers.

EXAMPLE 13

Breakage of Yeast Cells

Yeast cells were washed three times with 1 mM potassium phosphate buffer (pH 7.0) and resuspended in the same buffer with final concentration of $2 \times 10^{-9}$ cells/ml. 10 ml of cell suspension was nebulized for each experiment with nebulizer device 30 of FIGS. 7B and 7C. Three different pressures were employed (100, 200, and 300 PSI) with either $N_2$ or He. After nebulization, liquid in the upper chamber was returned to the lower chamber and a 1 ml sample was removed. The nebulization process was repeated for three cycles. Samples were centrifuged and the amount of protein released into the, supernatant were determined by Bradford Assay ($OD_{595}$). The results indicate that He is more effective than $N_2$ to break cells at higher pressures.

While the invention has been illustrated and described in detail in the figures and foregoing description, the same is to be considered as illustrative and not restrictive in character, it being understood that only the preferred embodiments have been shown and described and that all changes and modifications that come within the spirit of the invention are desired to be protected.

What is claimed is:

1. In a process for fragmenting a biomaterial and isolating and recovering a component thereof, the improvement comprising performing said fragmenting by nebulizing a liquid containing said biomaterial, said nebulizing including directing the liquid containing the biomaterial against a nebulization barrier so as to cause the biomaterial to be fragmented.

2. A process according to claim 1, wherein said, nebulizing includes repeatedly nebulizing said liquid.

3. A process according to claim 1, and also including recovering said component in a substantially pure form.

4. A process according to claim 1, wherein said biomaterial is DNA, a starch polymer, or a cell.

5. A process according to claim 1, wherein said biomaterial is a cell and said component is a cell subfraction.

6. A process according to claim 5, wherein said cell subfraction is DNA, a protein or a cell organelle.

7. A process according to claim 6, wherein said cell subfraction is a protein.

8. A process according to claim 6, wherein said cell subfraction is DNA.

9. A process according to claim 6, wherein said cell subfraction is a cell organelle.

10. A process according to claim 9, wherein said cell organelle is a nucleus, mitochondrion, or a chloroplast.

11. A process for fragmenting isolated DNA, comprising the step of nebulizing a liquid containing said DNA wherein said nebulizing takes place in a device which has a liquid input and a liquid output, wherein said device also comprises means for returning the liquid from the output to the input.

12. A process according to claim 11, and also comprising the step of recovering said DNA after said nebulizing.

13. A process according to claim 12, and also including the step of repairing the ends of said DNA after said recovering.

14. A process according to claim 11, wherein said DNA is substantially pure.

15. A process according to claim 14, wherein said nebulizing includes repeatedly nebulizing said liquid.

16. A process according to claim 11, and also comprising the step of including an agent in said liquid to increase its viscosity.

17. A process according to claim 11, wherein said liquid includes water.

18. A process according to claim 17, wherein said viscosity-increasing agent is a sugar or an alcohol.

19. A process according to claim 18, wherein said viscosity-increasing agent is glycerol, ethylene glycol or sucrose.

20. A process according to claim 19, wherein said DNA is included in sufficient amounts whereby self-protection provides larger final DNA fragments.

21. A process according to claim 19, wherein a suitable polymer is included in said liquid in an amount whereby said DNA is protected and larger fragments are obtained.

22. A process for determining a sequence of a DNA strand, comprising the steps of (i) nebulizing a liquid containing multiple copies of the DNA strand to thereby form DNA fragments, said nebulizing including directing the liquid containing the copies of the DNA strand against a nebulization barrier so as to cause the copies of the DNA strand to be fragmented, and (ii) determining by analysis of said fragments, a sequence of said DNA strand.

23. A process for producing DNA fragments, comprising repeatedly nebulizing liquid containing DNA, said nebulizing including directing the liquid containing DNA against a nebulization barrier, to thereby produce DNA fragments of ±200 base pairs at an efficiency of at least about 30%.

24. A process according to claim 23, wherein said efficiency is at least about 50%.

25. In a process for fragmenting a cell, the improvement comprising performing said fragmenting by nebulizing a liquid containing said cell, said nebulizing including directing the liquid containing the cell against a nebulization barrier so as to cause the cell to be fragmented.

26. A process according to claim 25 further comprising recovering a component of the cell in a substantially pure form.

27. A process according to claim 26, wherein said component is a protein.

28. A process according to claim 27, wherein said component is DNA.

29. A process according to claim 28, wherein said component is a cell organelle.

* * * * *

UNITED STATES PATENT AND TRADEMARK OFFICE
CERTIFICATE OF CORRECTION

PATENT NO.   : 5,610,010
DATED        : March 11, 1997
INVENTOR(S)  : Stefan J. Surzycki et al.

It is certified that error appears in the above-indentified patent and that said Letters Patent is hereby corrected as shown below:

In col. 4, line 28, please delete "exploded-cross" and insert in lieu thereof --exploded cross--.

In col. 6, line 12, please delete "ethylenesglycol" and insert in lieu thereof --ethylene glycol--.

In col. 14, line 34, please delete "," after "the".

In col. 14, line 52, please delete "," after "said".

In col. 16, line 27, please delete "27" and insert in lieu thereof --26--.

In col. 16, line 29, please delete "28" and insert in lieu thereof --26--.

Signed and Sealed this

Third Day of February, 1998

BRUCE LEHMAN

*Attest:*

*Attesting Officer*

*Commissioner of Patents and Trademarks*